United States Patent [19]
Olsen

[11] Patent Number: 5,207,109
[45] Date of Patent: May 4, 1993

[54] INTERNAL-EXTERNAL SAMPLE INJECTOR

[75] Inventor: Kristine Olsen, Richmond, Calif.

[73] Assignee: Rheodyne, Inc., Cotati, Calif.

[21] Appl. No.: 652,083

[22] Filed: Feb. 7, 1991

[51] Int. Cl.$^5$ ............................................. G01N 1/00
[52] U.S. Cl. .............................................. 73/863.73
[58] Field of Search ............ 73/863.72, 863.73, 864.83, 73/864.84; 422/103

[56] References Cited
U.S. PATENT DOCUMENTS

| | | |
|---|---|---|
| 3,961,534 | 6/1976 | Gundelfinger . |
| 4,182,184 | 1/1980 | Bakalyar et al. . |
| 4,506,558 | 3/1985 | Bakalyar . |
| 4,726,237 | 2/1988 | Yung ............................ 73/863.73 |

Primary Examiner—Robert Raevis
Attorney, Agent, or Firm—Arthur Freilich; Robert D. Hornbaker; Leon D. Rosen

[57] ABSTRACT

A sample injector is provided, which enables changing of the volume of the sample chamber between a very small volume and larger volumes. The injector includes a housing, a stator (16, FIG. 3) mounted in the housing, and a rotor (26) pivotally mounted in the housing, with the stator and rotor having facewise adjacent faces extending perpendicular to the pivot axis. First and second stators are alternately mountable in the housing, with the first stator having a disc element (44, FIG. 3) that includes a storage channel (62) in one of its faces to form an internal storage chamber of small volume. The other, alternate stator has at least one disc element (44X, FIG. 5) that includes a pair of through passages (52X, 56X) therein that are constructed to connect to sample ports (52, 56) of a disc element that hold the opposite ends of an external sample loop (90) to enable the injector to be used with a larger storage volume.

8 Claims, 3 Drawing Sheets

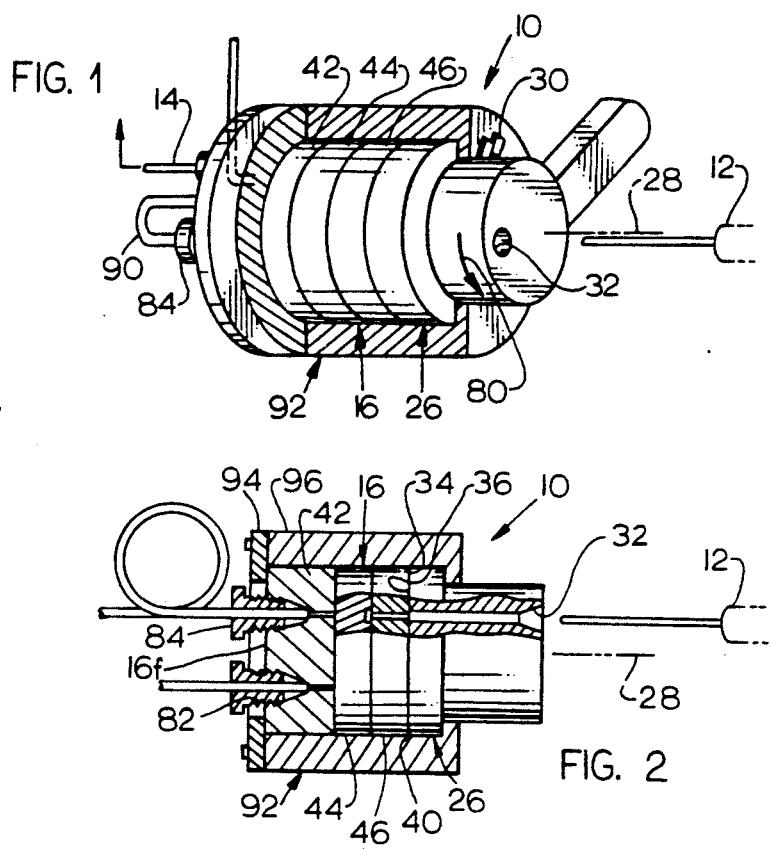
FIG. 1
FIG. 7
FIG. 2
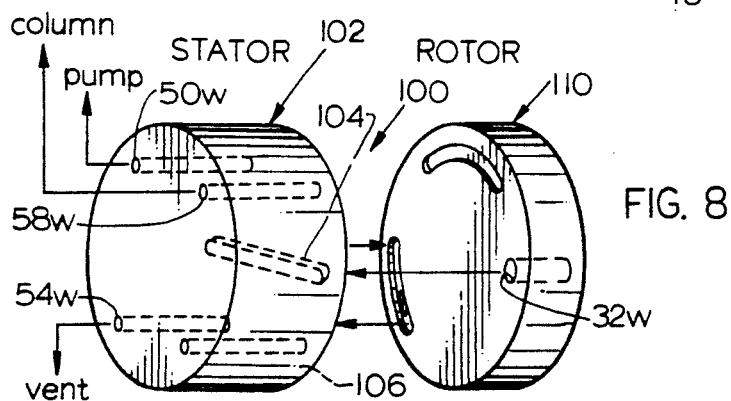
FIG. 8
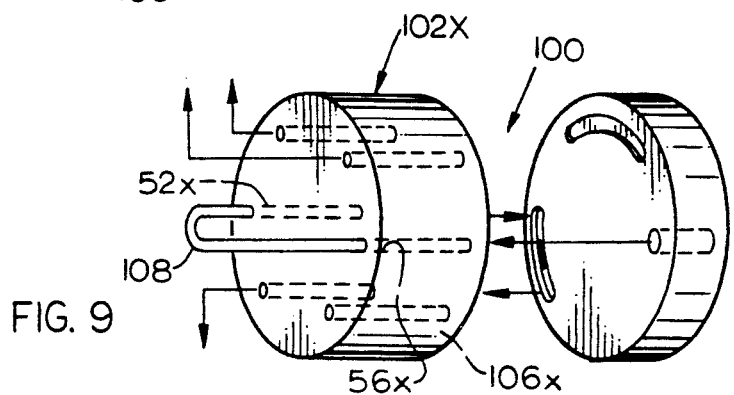
FIG. 9

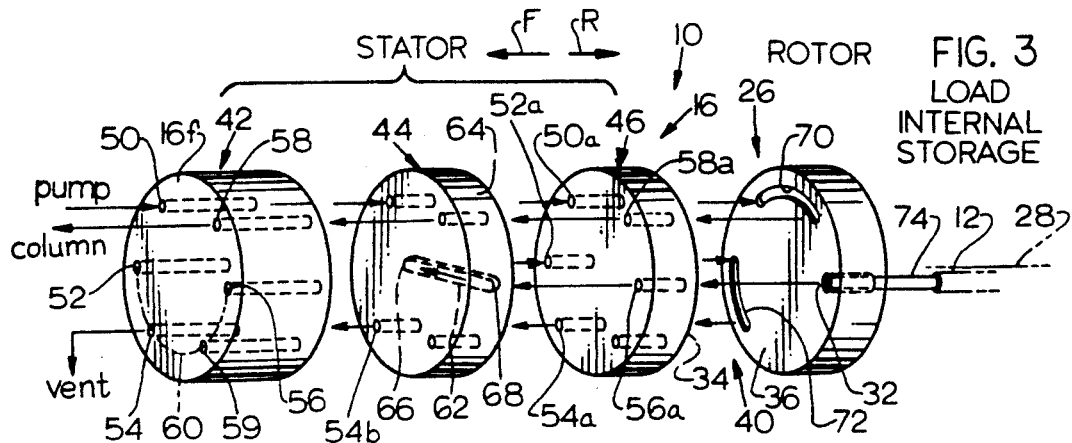
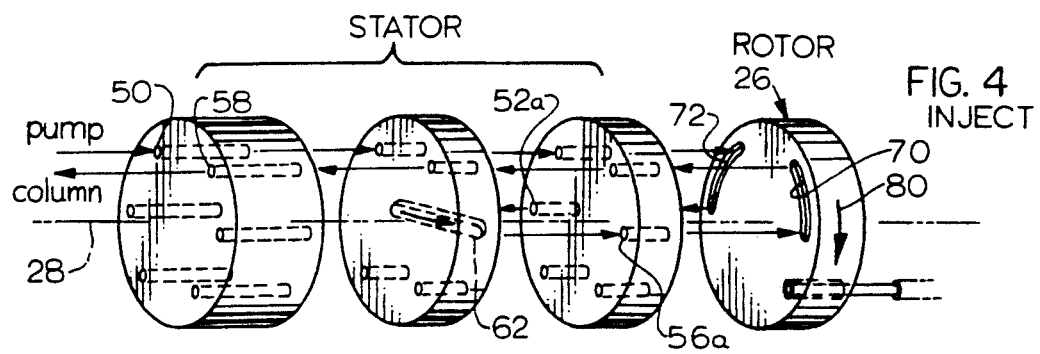
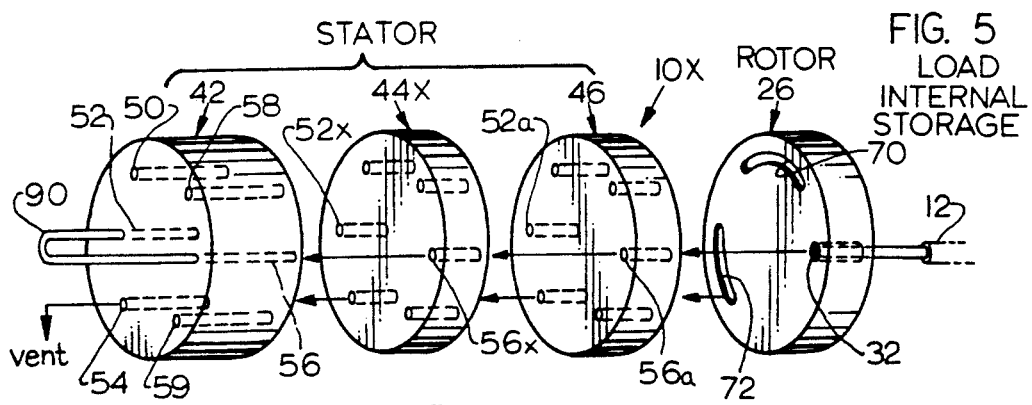
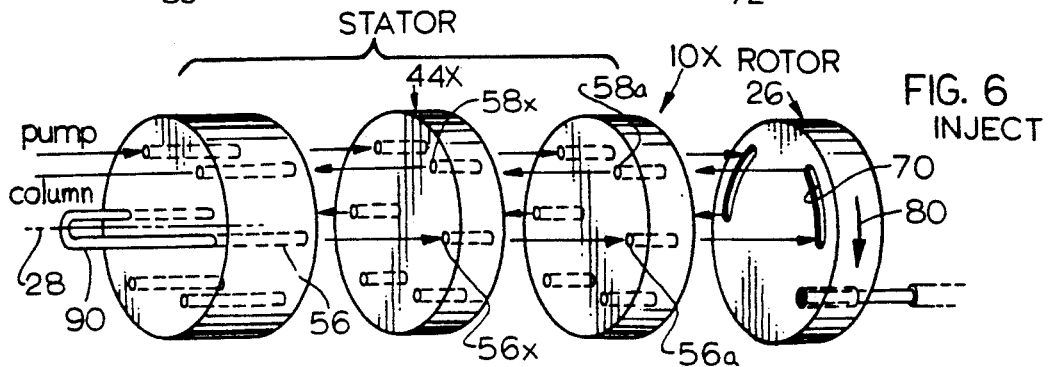

INTERNAL-EXTERNAL SAMPLE INJECTOR

BACKGROUND OF THE INVENTION

In the practice of liquid chromatography and other analytical methods involving flowing liquid streams, a sample injector is often used. A sample injector receives a liquid sample from a syringe, and when switched, transfers the sample at high pressure into a chromatographic column. One successful type of injector includes a largely disc or cylinder-shaped rotor with a passage extending therethrough that receives a syringe needle. The rotor has a face extending perpendicular to its axis of rotation, which lies facewise adjacent to the face of the stator. The stator has passages therethrough which connect to an external sample loop. When the syringe needle is inserted into the rotor and operated, the sample fills (fully or partially, depending on the technique chosen) the volume of the sample loop and of the stator passages connected to the loop. When the rotor is turned, solvent from a high pressure pump pumps the sample through the loop and corresponding stator passages into the chromatographic column. U.S. Pat. Nos. 4,182,184 and 4,506,558, both by Bakalyar, describe injectors of this type, that are devoid of any passage between the syringe needle and loop that would waste part of the sample.

If the sample is larger than the volume of the external sample loop (plus the small additional volume of the two stator passages and one rotor groove), then the volume of sample injected into the column is precisely controlled by the size of the sample loop. Different size sample loops can be used, where different sizes of samples are to be injected. However, for very small volumes that are to be injected, the volume occupied by the passages plus the smallest length of sample loop which can connect the two passages, may be too great. It would be desirable if a sample injector were available which could store and inject a predetermined precise volume which was very small. It would further be desirable if such an injector could be readily changed between a configuration for injecting a very small volume, and configurations for injecting one or more much larger volumes.

SUMMARY OF THE INVENTION

In accordance with one embodiment of the present invention, a sample injector is provided, which can be operated to inject a very small predetermined sample volume. The injector can also be switched to configurations for injecting larger volumes. The injector includes a stator and rotor having facewise adjacent faces, with the rotor being rotatably mounted on the stator about an axis extending normal to the faces. The stator includes at least one disc element with a storage channel formed in at least one face thereof, and with opposite ends of the channel positioned to align with openings in the rotor face. The sample storage channel formed in a disc element, allows injection of a predetermined sample size which is very small. The disc element forming the storage channel can be replaced, so that the stator passes the sample to an external sample loop of desired size, for injecting larger samples of predetermined sizes.

The novel features of the invention are set forth with particularity in the appended claims. The invention will be best understood from the following description when read in conjunction with the accompanying drawings.

BRIEF DESCRIPTION OF THE DRAWINGS

FIG. 1 is a partially sectional isometric view of a sample injector constructed in accordance with one embodiment of the present invention.

FIG. 2 is a sectional side view of the injector of FIG. 1.

FIG. 3 is a simplified exploded isometric view of the injector of FIG. 1, shown in an internal storage configuration, and in a load position.

FIG. 4 is a view similar to that of FIG. 3, but with the injector an inject position.

FIG. 5 is a view of the injector of FIG. 3, but reconfigured to an external storage configuration, and also shown in a load position.

FIG. 6 is a view similar to that of FIG. 5, but with the injector in an inject position.

FIG. 7 is a isometric view of another middle stator disc element which can substitute for that of FIG. 1.

FIG. 8 is an exploded isometric view of an injector constructed in accordance with another embodiment of the invention, shown in an internal storage configuration.

FIG. 9 is a view similar to that of FIG. 8, but with the stator replaced so the injector is in an external storage configuration.

DESCRIPTION OF THE PREFERRED EMBODIMENTS

Figure 10:
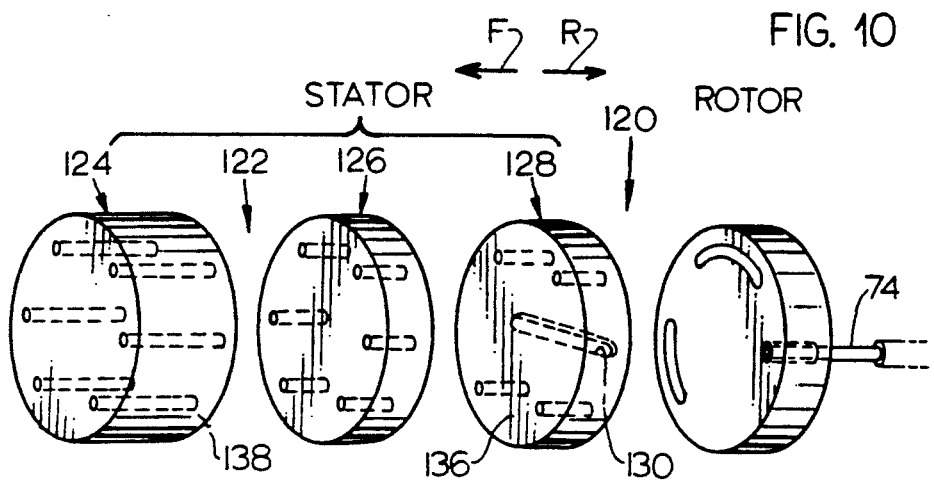
FIG. 10 is a simplified exploded isometric view of an injector constructed in accordance with another embodiment of the present invention, in an internal storage configuration, and in a load position.

FIG. 1 illustrates a sample injector 10 of the present invention, which can receive a small sample from a micro syringe 12 or other loading device, and deliver a predetermined volume of the sample from a column outlet 14 to a chromatographic column or other analytical device. Although the volume of the sample may not be accurately known, so long as it is much greater than the storage volume in the injector, a precisely repeatable volume will be injected. For example, if the storage volume in the injector 10 is precisely 10 uL (microliters) and the volume of sample delivered from the syringe 12 is greater than 30 uL then the injector will inject precisely 10 uL of sample into the column.

The injector includes a stator 16, which comprises three stator disc elements 42, 44, and 46, and also includes a rotor 26. The rotor can pivot about an axis 28, with stops 30 limiting the rotor to pivoting by a predetermined angle such as 60 degrees. In one angular position of the rotor, the injector is in a load position at which a sample is loaded through a sample-receiving port 32 into the injector. At the other angular position of the rotor when it has been pivoted by 60 in the direction of arrow 80, it is in an inject position at which the sample is injected under high pressure into the column.

As shown in FIG. 3, which is a rear view instead of the front one of FIG. 1, the stator and rotor have adjacent faces 34, 36 that form an interface 40 between them. The stator 16 is formed of the three disc elements which include a main or forward stator disc element 42, a middle stator disc element 44, and a rear stator disc element 46. In order to aid in describing the injector, forward and rearward directions along the axis 12 are indicated by arrows F and R. The rotor 26 lies rearward of the stator 16.

The forward end 16f of the stator provides access to five passages or ports 50-58 (a sixth one 59 also can be provided). For the internal storage configuration of FIGS. 3 and 4, the external loop ports 52, 56 are not used. One port 50 receives a mobil phase liquid from a pump at a high pressure such as 5,000 psi. Another port 58 leads to the chromatographic column into which fluid is injected at high pressure. Another port 54 is connected to a venting device through which fluid can be discharged and usually discarded. All of the ports lie on an imaginary circle 60 that is concentric with the pivot axis 28 of the rotor.

The middle stator disc element 44 forms an internal storage chamber 62 in the form of a channel in the rearward face 64 of the element. The opposite ends 66, 68 of the internal storage chamber are aligned with the sample or external ports 52, 56 in the forward disc element, but do not communicate with it. That is, the ends 66, 68 of the storage chamber are at the same rotational positions about the pivot axis 28 as the loop ports 52, 56. The opposite ends 66, 68 of the storage chamber are angularly spaced by 180° about the pivot axis 28, which is more than twice the spacing of adjacent stator ports. The rearward stator disc element 46 has five ports or passages 50a-58a in line with the ports 50-58 of the forward disc element 42. The rotor 26 includes the sample receiving port or passage 32 and forms a pair of interconnect channels 70, 72 in its forward face 36 that can connect pairs of ports 50a-58a of the stator disc element 46.

To analyze a sample originally contained in the syringe 12, the syringe loading needle 74 is inserted into the rotor port 32 until the tip of the needle abuts the face 34 of the rearward disc element 46. The syringe is operated to transfer the sample forwardly through the port 56a, sidewardly through the internal storage chamber 62, and rearwardly through the port 52a. The pressure applied by the syringe is generally less than a few (three) hundred psi, which is much less than over 1000 psi typically applied by a pump that pumps the sample into a column. The volume of the internal storage chamber 62 plus the volume of channel 72 and ports 52a and 56a equals the total internal storage volume. During operation of the syringe 12, solvent previously filling the internal storage volume is displaced through the vent port 54. Such solvent plus the amount of any injected sample which is greater than the internal storage volume (of chamber 62 plus ports 52a, 56a and channel 72) passes through aligned ports 54a, 54b, and 54, and is vented. During sample loading, mobile phase fluid is pumped under high pressure into the pump port 50, through the interconnect channel 70, and out through the column port 58, to maintain a continuous flow into the column.

FIG. 4 shows the apparatus of FIG. 3 in an inject mode. The rotor 26 has been turned by 60 degrees in the direction of arrow 80 to shift the interconnect channels 70, 72. The high pressure mobil phase fluid pumped into the port 50 now passes through the interconnect channel 72 through the port 52a, internal storage chamber 62, and port 56a, to displace all of the sample lying in the internal storage volume of the injector. The sample passes through the rotor channel 70 and out through the column port 58 to the chromatographic column in order to be analyzed.

By forming the storage chamber 62 in one of the disc elements of the stator, applicant is able to achieve a very low internal storage volume, such as less than 5 uL (microliters). In previous injectors of this type, where an external sample loop was used, the volume required to fill the sample loop and those ports or passages which also store the sample, generally exceeded 5 uL.

Of the three disc elements 42-46 of the stator, the rearward element 46 is formed of a very hard material such as ceramic, so that its face 34 is not scratched when the tip of the needle 74 abuts the face and scrapes along the face as the rotor is turned by 60 degrees. The main or forward disc element 42 is generally formed of a machineable material such as stainless steel, to facilitate connection to external tubes such as those leading to the pump, the column, and a vent for disposing of solvent and excess sample. As shown in FIG. 2, threads 82 are generally formed in the ports of the forward disc element 42, in its forward face 16f, to enable fittings such as 84 to be installed. The middle disc element 44 (FIG. 3) serves as a seal between the forward and rearward elements 42, 46, with the middle element 44 generally formed of a polymer suitable for sealing. Applicant prefers to form the internal storage chamber 62 in a face of the middle element 44, because it is easier to machine the element 44. Also, by locating the channel internal to the stator, applicant avoids the buildup of debris in the storage chamber that is generated where faces slide across one another. However, as described below, it is also possible to form a channel in the rearward element 46, even in its rearward face, although forming a channel in ceramic material is more expensive.

Where a larger sample storage volume is required, the injector is preferably modified to the configuration shown at 10X in FIGS. 5 and 6. The configuration 10X of FIG. 5 is identical to the configuration 10 of FIG. 3, except that a different middle stator disc element 44X is substituted for the element 44 of FIG. 3. Also, an external sample loop 90 is connected between the sample ports 52, 56 of the forward disc element 42. The alternate middle disc element 44X does not have an a radial groove forming an internal storage chamber, but instead has a pair of sample loop coupling ports or passages 52x, 56x in line with the forward disc element loop ports 52, 56. As a result, when the syringe 12 is installed in the sample-receiving port 32 of the rotor and transfers a sample into the injector, the sample passes forwardly through the aligned ports or passages 56a, 56x, 56 of the disc element into the external sample loop 90 and from there passes rearwardly through the ports 52, 52x, and 52a and channel 72. Excess sample and any mobile phase fluid previously in the ports passes through other ports out through the vent port 54.

When the injector 10X is in its inject position shown in FIG. 6, the rotor has been turned along the arrow 80 by 60 degrees. The stored sample in the loop 90 is then pumped at high pressure, rearwardly through ports 56, 56x, 56a and 52, through interconnect channel 70, and forwardly through ports 58a, 58x and 58 into the chromatographic column. The external storage volume is much larger than the internal storage volume of the configuration of FIG. 3, with the external storage volume being variable by varying the size of the storage loop 90. When a person Wishes to inject a larger volume of at least about 5 uL to 5 mL (milliliters) or more, he switches the configuration of the injector by changing the middle disc element and installing the external sample loop 90. The other parts of the injector are the same, so the additional cost for the convertible injector is primarily equal to the cost of one of the middle disc elements such as 44x.

As indicated in FIGS. 1 and 2, one configuration of an injector of the invention includes a housing 92 which retains the three disc elements of the stator as well as the rotor 26 to keep them tightly pressed against one another while allowing rotation of the rotor. Also, the housing is constructed so the middle disc element can be removed and replaced. A wide variety of housing configurations can be used, such as one wherein an end plate 94 of the housing can be removed from the rest 96 of the housing, as with screws, to replace the middle disc element. It should be noted that while the disc elements may be of simple disc shape, they may have other configurations, so long as their adjacent faces can seal to one another and the faces 34, 36 and the interface 40 extend perpendicular to the axis of rotation 28 of the rotor. It also should be noted that while the sample loop coupling passages 52x, 56x preferably extend parallel to the axis 28, they could extend at an angle to it, in which case the rear ends of the passages would be aligned with the sample ports 52, 56 only with a small offset.

FIG. 7 is a view of another middle stator disc element 44Y which can be substituted for the disc element 44 of FIG. 3. The figure shows the rearward face 64y of the element, in which an internal storage chamber channel 62y has been formed. The channel does not extend in a straight line but has changes in direction. Such a nonlinear channel has the advantage that it promotes radial convective mixing and/or turbulence, which tend to reduce the dispersion effects inherent in laminar flow. Also, the volume of the channel 62y is increased somewhat over the volume of the channel 62 in FIG. 3, although it is still less than achieved with the smallest external sample loop. The shape, length, depth, and width of the channel are thus variable to allow choosing a volume within a wide range and/or to allow optimization of dispersion characteristics.

FIGS. 8 and 9 illustrate another injector 100 wherein the stator 102 includes a single disc element. The disc element has an internal storage chamber 104 in the form of a groove in the rearward face 106 of the element. The rotor 110 is of the same construction as that of FIG. 3. The same stator element 102 forming the storage groove 104 also forms ports 50w, 58w, and 54w leading to a pump, a column, and a vent. To convert the injector to one with a larger storage volume, the element 102 is replaced by an element 102X, shown in FIG. 9, which does not have a channel in its rearward face 106x, but which has a pair of ports 52x, 56x that can connect to an external sample loop 108. While the stator element 102 of FIG. 8 is of conceptually simple construction and can store a very small sample volume, it also has practical disadvantages. In order to avoid scratching the rear face 106 of the stator element by a needle in the rotor port 22w, the stator, or at least its face, must be constructed of a material harder than that of a typical stainless steel syringe needle, such as a ceramic. It has been costly to form a channel in such hard material. Also, fittings or other connectors that must be installed at the front ends of ports 52x, 56x of the stator element 102x are more difficult to install if there are not threaded holes in the stator front face. Of course, forming such threaded holes in a ceramic material is very costly. Other connector arrangements can be used but they are not as convenient as threaded fittings.

Figure 11:
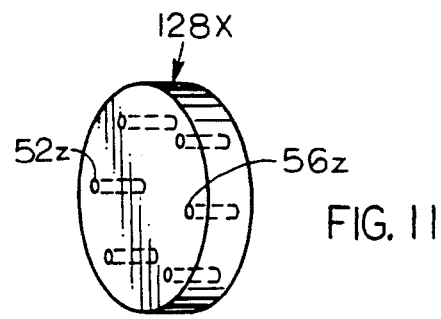
FIG. 11 is an isometric view of a substitute disc element, which can be substituted for the rearmost disc element of the injector of FIG. 10 to convert to an external storage configuration.

FIG. 10 illustrates still another injector 120, which includes a stator 122 with three disc elements 124-128. The internal storage chamber groove 130 is formed in the rearmost disc element 128. This is the advantage that the internal storage volume equal only the volume of the groove 130 and of one of the rotor channels, but not the volume of passages leading through another disc element to and from the groove 130. A disadvantage of this arrangement is that, since the rear element 128 must be made of a hard material such as ceramic, or at least its face must be made of hard material, to avoid scratching by the injector needle 74, it can be expensive to form the groove 130. The frontmost disc element 124 can be made of a machineable material such as stainless steel, in which threads can be formed for connection to fittings leading to a pump, a column, a vent, and the opposite ends of a sample loop. The middle disc element 126 serves to seal the closest faces 136, 138 of the rear-most and frontmost elements, and can be formed of a polymer. FIG. 11 illustrates a substitute disc element 128X which can be substituted for the element 128. The element 128X has through ports therein at 52z, 56z at positions corresponding to the opposite ends of the channel 130 in the disc element 128.

Figure 12:
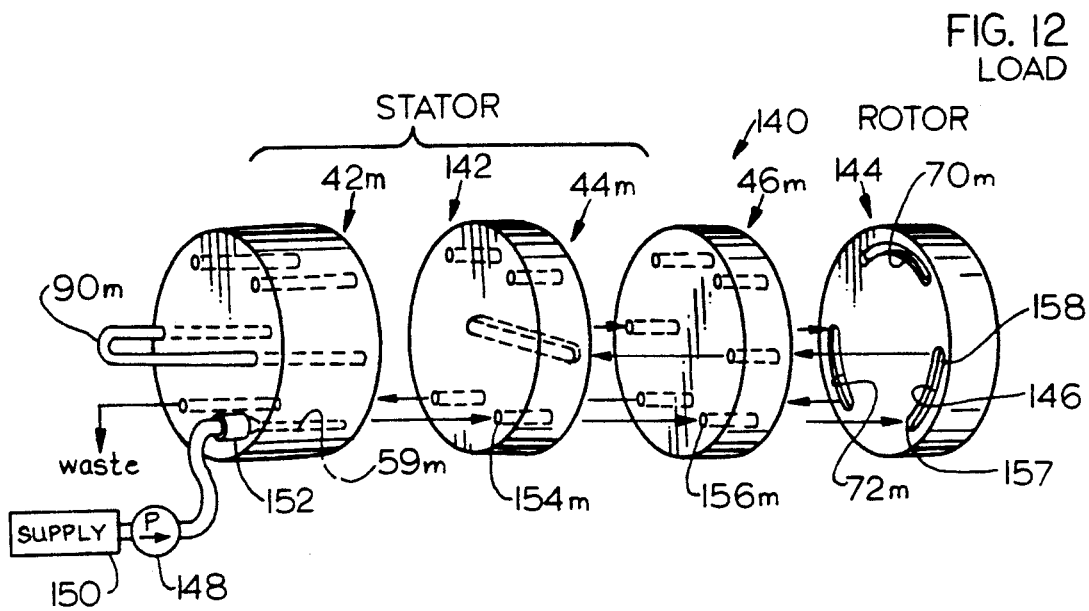
FIG. 12 is a simplified exploded isometric view of an injector constructed in accordance with another embodiment of the invention, which does not require syringe loading, shown in a load position.

FIG. 12 shows an injector 140 of a construction similar to the injector of FIG. 3. However, the injector 140 is designed to be loaded through an end of its stator 142 rather than through any syringe-receiving port in its rotor 144. The rotor 144 is similar to the rotor 26 of FIG. 3 except that rotor 144 has a third channel 146, in addition to its interconnect channels 70m, 72m. The stator 142 has three stator disc elements 42m, 44m, and 46m that are similar to that of FIG. 3 except that the port 59m in end disc 42m forms an inlet designed to receive a sample to be injected.

The injector 140 can be loaded by a variety of fluid sources, including a syringe with or without a needle, a pump, etc. FIG. 12 shows a pump 148 which pumps fluid from a supply 150 through a fitting 152 on the end disc element 42m. The fluid is pumped through aligned ports 59m, 154m, 156m in the stator disc elements, into one end 157 of the rotor channel 146, and out through an opposite end 158 of the channel. The channel end 158 lies at the same position as the needle-receiving port 32 of the injector of FIG. 3. After injected fluid reaches the channel end 158, it follows the same course as fluid loaded into the injector of FIG. 3.

The injector of FIG. 12 has the advantage that it can be loaded by a variety of sources, but has the disadvantage that some sample is lost in the volume of the loading ports 59m, 154m, 156m and the loading channel 146. When the sample is loaded, the rotor is turned 60° so the channels 70m, 72m are aligned with certain ports in the same manner as shown in FIG. 4 for injection.

If the volume of the sample is large, the disc element 44m of FIG. 12 can be replaced by the disc element 44X of FIG. 5, which allows an external storage loop 90m to be used.

Thus, the invention provides an injector which has a very small internal sample storage volume, that can be loaded with minimal or no wastage of sample from a syringe needle. Also, the injector can be converted at minimal cost into one that uses an external storage loop of much larger volume. The injector includes a rotor, pivotal about an axis with respect to a stator, and with stator and rotor having faces extending perpendicular, or normal to the axis. The stator has a disc element (which may not be of simple disc shape) with a channel in at least one face thereof, which stores the sample to be injected. The opposite ends of the internal storage channel are coupled either directly or through ports in another stator disc, to a rotor needle-receiving port and to inter- connect channels in the rotor, or through ports to an inlet in a stator end disc. The stator can include a plurality of disc elements, with the storage channel formed in a selective one of them, or the stator can include a single disc element.

Although particular embodiments of the invention have been described and illustrated herein, it is recognized that modifications and variations may readily occur to those skilled in the art, and consequently, it is intended that the claims be interpreted to cover such modifications and equivalents.

I claim:

1. In an injector apparatus which includes a housing having a pivot axis and a rotor pivotally mounted in the housing to pivot about said axis between load and inject positions, and wherein the injector is constructed to hold a first stator having pump, column, and vent ports and first and second sample loop locations, with the rotor having first and second interconnect channels at the rotor-stator interface, the first channel positioned to connect the pump and column ports at the load position and to connect the column port and first sample loop location at the inject position, and the second channel is positioned to connect the second sample loop location and the vent port in the load position and to connect the second sample location and the pump port in the inject position, the improvement wherein:

said first stator has at least one disc element with opposite faces and with a storage channel in at least one of said faces, said storage channel having opposite ends at the same rotational positions about said axis as said first and second sample loop locations, whereby to effectively hold a very small sample; and including a second stator which is mountable in said housing in place of said first stator, said second stator having at least one second disc element with opposite faces and walls forming first and second sample loop passages lying at the same rotational positions about said axis as said first and second sample loop locations, each of said sample loop passages extending completely through said second disc element, and through said entire second stator, whereby to connect to the sample loop ports of the stator and through them to an external sample loop so as to effectively hold a larger sample.

2. The improvement described in claim 1 wherein:

said stators each includes a rear disc element, one of two different middle disc elements, and a front disc element, said rear and front disc elements being the same in both said first and second stators, with each of said front disc elements forming said first and second sample loop ports;

said first stator comprises a first of said middle disc element that forms said storage channel with said storage channel having opposite ends, and said second stator comprises a second of said middle disc element that replaces said first middle disc element, said second middle disc element forming portions of each of said sample loop passages.

3. A sample injector apparatus for receiving a sample to be analyzed from a loading needle, and transferring the sample to an analyzing instrument, comprising:

a stator having a face;

a single rotor having a face, said rotor pivotally coupled to said stator about an axis to pivot between load and inject positions, with said faces lying adjacent to each other and facing axially at an interface;

said stator having a plurality of ports open to said stator face and lying on an imaginary circle concentric with said axis;

said rotor having a needle-receiving passage open to said stator face and having first and second interconnect channels each connecting a pair of said stator ports;

said stator forming an elongated sample storage chamber;

said ports and interconnect channels being arranged so in said load position of said rotor, fluid injected through said needle-receiving passage of stator enters said storage chamber and fluid passes in a first direction through said storage chamber and through one of said interconnect channels at said interface and into one of said stator ports, and in said inject position of said rotor fluid passes through one of said interconnect channels and in an opposite second direction through said storage channel and through the other of said interconnect channel and through another of said ports of said stator to said analyzing instrument;

said interconnect channels each extending substantially along said imaginary circle between a pair of ports of said stator which lie along said imaginary circle;

said stator includes at least one disc element having opposite faces and said storage chamber comprising a storage chamber channel extending largely radially in said stator along at least one of said faces of said disc element, with opposite ends of said storage chamber channel spaced apart along said imaginary circle by at least twice the distance along said circle by which any pair of adjacent of said ports of said stator are spaced.

4. A sample injector apparatus for receiving a sample to be analyzed from a loading needle and transferring the sample to an analyzing instrument, comprising:

a stator having a rearward face;

a rotor having a forward face, said rotor pivotally coupled to said stator about an axis between load and inject positions, with said faces lying adjacent to each other and facing axially at an interface;

said stator having forward, middle, and rearward disc elements, said rearward and forward disc elements each having a plurality of aligned through passages lying on an imaginary circle concentric with said axis including a pump passage, a column passage, a vent passage, a first sample loop passage, and a second sample loop passage;

said middle disc element having pump, column and vent through passages aligned with said pump, column and vent passages of said forward and rearward disc elements, and said middle disc element having a sample storage chamber channel in a face thereof, with opposite ends of said storage channel aligned respectively with said first and second loop passages of said rearward disc element.

5. The injector apparatus described in claim 4 wherein:
   said stator is disassemblable so said middle disc element can be replaced; and including
   a replacement disc element which can replace said middle element, said replacement disc element having through passages positioned to be aligned with said pump passage, column passage, vent passage, first sample loop passage, and second sample loop passages of said rearward and forward disc elements.

6. The injector apparatus described in claim 4 wherein:
   said middle disc element is of a softer material than said rearward or forward disc elements, whereby to seal against them.

7. A sample injector apparatus for receiving a sample to be analyzed from a loading needle, and transferring the sample to an analyzing instrument, comprising:
   a stator having a face;
   a rotor having a face, said rotor pivotally coupled to said stator about an axis to pivot between load and inject positions, with said faces lying adjacent to each other and facing axially at an interface;
   said stator having a plurality of ports open to said stator face and lying on an imaginary circle concentric with said axis;
   said rotor having a needle-receiving passage open to said stator face and having first and second interconnect channels each connecting a pair of said stator ports;
   said stator forming an elongated sample storage chamber;
   said ports and interconnect channels being arranged so in said load position of said rotor, fluid injected through said needle-receiving passage of said stator enters said storage chamber and fluid passes in a first direction through said storage chamber and through one of said interconnect channels at said interface and into one of said stator ports, and in said inject position of said rotor fluid passes through one of said interconnect channels and in an opposite second direction through said storage chamber and through the other of said interconnect channels and through another of said ports of said stator to said analyzing instrument;
   an external sample storage loop;
   said stator includes a plurality of disc elements arranged in a stack with adjacent faces, with a first of said disc elements having a face forming said sample storage chamber with said sample storage chamber having opposite ends lying at different locations along said imaginary circle, and with a frontmost of said disc elements forming a pair of external sample loop ports for holding the ends of said external sample storage loop;
   said first disc element being removable from said stack; and including
   a replacement disc element which can replace said first disc element, said replacement disc element having a pair of through holes at locations corresponding to the opposite ends of said storage chamber, for carrying fluid to said external loop ports of said frontmost disc.

8. A sample injector apparatus for receiving a sample to be analyzed from a loading needle and transferring the sample to an analyzing instrument, comprising:
   a stator having a rearward face;
   a rotor having a forward face, said rotor rotatably mounted with respect to said stator about an axis between load and inject positions, with said faces lying adjacent to each other and facing axially at an interface, said rotor having a needle-receiving through passage and first and second interconnect channels formed in said rotor forward face;
   said stator having a pump passage, a column passage, and vent passage all extending completely through said stator, and said stator having a sample storage chamber channel with first and second opposite ends in its rearward face, with said first channel end aligned with said rotor needle-receiving passage and said second channel end aligned with a first of said interconnect channel in said load position;
   said stator is replaceable, and including
   a replacement stator element which has through passages at locations corresponding to said pump passage, said column passage, said vent passage, said first end of said storage chamber channel, and said second end of said storage chamber channel, with the through passages of said replacement stator element that correspond to the locations of said channel ends, being isolated from each other so fluid cannot flow between them within said replacement stator element.

* * * * *